United States Patent
Faltenbacher et al.

(10) Patent No.: US 9,950,880 B2
(45) Date of Patent: Apr. 24, 2018

(54) METHOD AND DEVICE FOR FITTING INJECTION-MOLDED PARTS

(71) Applicant: HEKUMA GMBH, Eching (DE)

(72) Inventors: Christian Faltenbacher, Eching (DE); Manuel Hilpert, Eching (DE); Konrad Hintermaier, Eching (DE)

(73) Assignee: HEKUMA GMBH, Eching (DE)

( * ) Notice: Subject to any disclaimer, the term of this patent is extended or adjusted under 35 U.S.C. 154(b) by 0 days.

(21) Appl. No.: 14/776,360

(22) PCT Filed: Mar. 14, 2014

(86) PCT No.: PCT/EP2014/055121
§ 371 (c)(1),
(2) Date: Dec. 1, 2015

(87) PCT Pub. No.: WO2014/140290
PCT Pub. Date: Sep. 18, 2014

(65) Prior Publication Data
US 2016/0083201 A1 Mar. 24, 2016

(30) Foreign Application Priority Data
Mar. 14, 2013 (DE) .................. 10 2013 204 425

(51) Int. Cl.
*H01L 21/677* (2006.01)
*B65G 65/44* (2006.01)
(Continued)

(52) U.S. Cl.
CPC ............ *B65G 65/44* (2013.01); *B01L 3/0275* (2013.01); *B65G 47/34* (2013.01); *B01L 2200/12* (2013.01);
(Continued)

(58) Field of Classification Search
CPC ........ B65G 27/04; B65G 27/06; B65G 27/10; B65G 27/12; B65G 29/00; B65G 47/12; B65G 47/14; B65G 47/1407; B65G 47/145; B65G 47/34; B65G 65/44; H01L 21/67271; H01L 21/673; H01L 21/67371
See application file for complete search history.

(56) References Cited

U.S. PATENT DOCUMENTS 4,395,184 A * 7/1983 Braden .................... B05D 1/00
29/759
7,861,889 B2 * 1/2011 Ishigure ............. B65G 47/1428
198/393

FOREIGN PATENT DOCUMENTS

DE 38 39 892 A1 6/1989
DE 37 42 586 A1 7/1989
(Continued)

*Primary Examiner* — Mark J Beauchaine
(74) *Attorney, Agent, or Firm* — Horst M. Kasper, Esq

(57) ABSTRACT

The invention relates to a device for orienting elements, in particular filter elements (F), for fitting injection-molded parts, in particular pipette tips (P), comprising an accommodating container (1a) for accommodating the filter elements (F) as bulk material, a sieve plate (1), which forms the bottom of the accommodating container and which has bores (11) for accommodating individual filter elements (F), a buffer plate (2), which is arranged under the sieve plate (1) and which has bores (2.1) corresponding to the bores of the buffer plate (2) and which is arranged below the buffer plate in such way that the transfer plate can moved in relation to the buffer plate (2).

14 Claims, 4 Drawing Sheets

Figure 3:
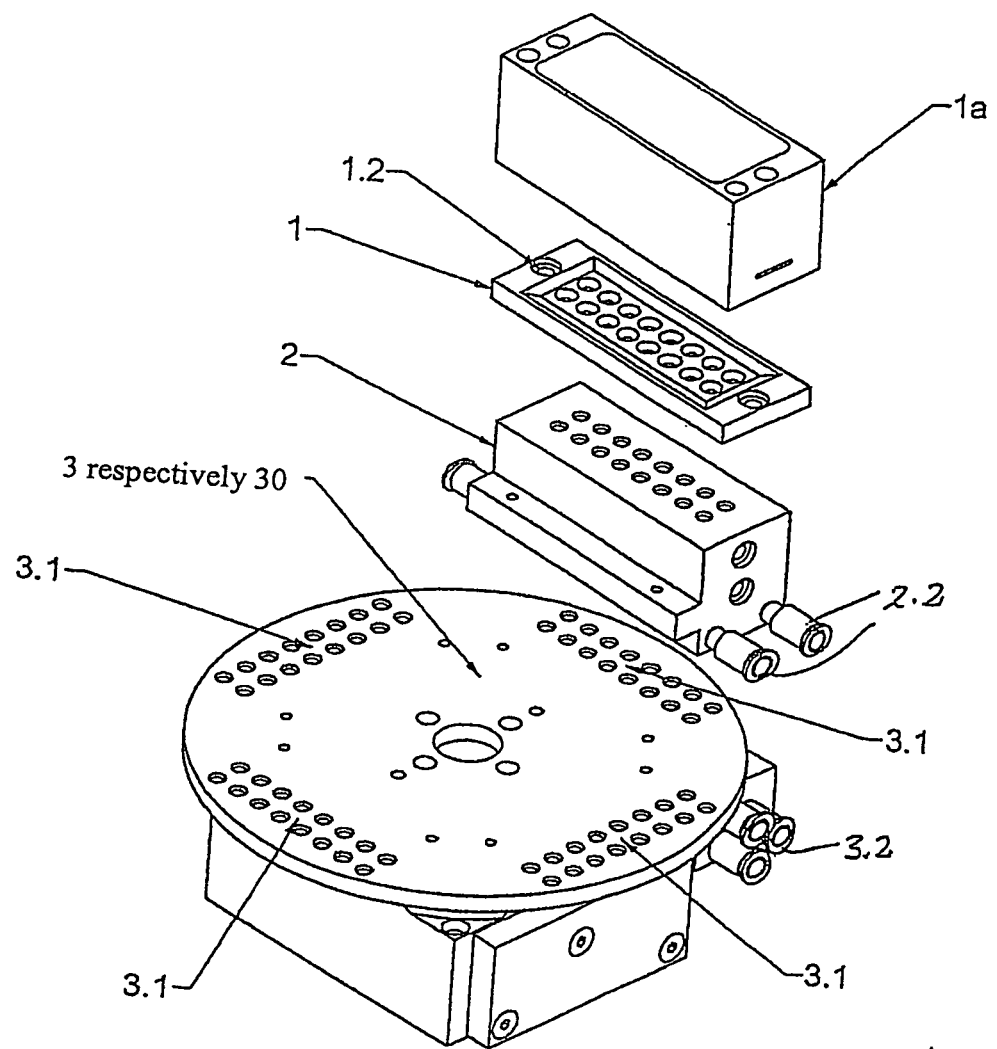

(51) Int. Cl.
    *B01L 3/02*        (2006.01)
    *B65G 47/34*     (2006.01)
    *B29C 45/72*      (2006.01)
    *B29C 31/00*      (2006.01)

(52) U.S. Cl.
    CPC ..... *B01L 2300/0681* (2013.01); *B29C 31/008* (2013.01); *B29C 2045/7242* (2013.01); *B29C 2945/76357* (2013.01)

(56) References Cited

FOREIGN PATENT DOCUMENTS

| | | |
|---|---|---|
| DE | 100 34 160 A1 | 1/2002 |
| DE | 20 2012 005 247 U1 | 6/2012 |
| EP | 0135 372 A2 | 3/1985 |
| GB | 485 251 A | 5/1938 |
| JP | S 54 13194 U | 1/1979 |
| JP | H 03 120 124 A | 5/1991 |
| WO | WO 2011/003507 A1 | 1/2011 |

\* cited by examiner

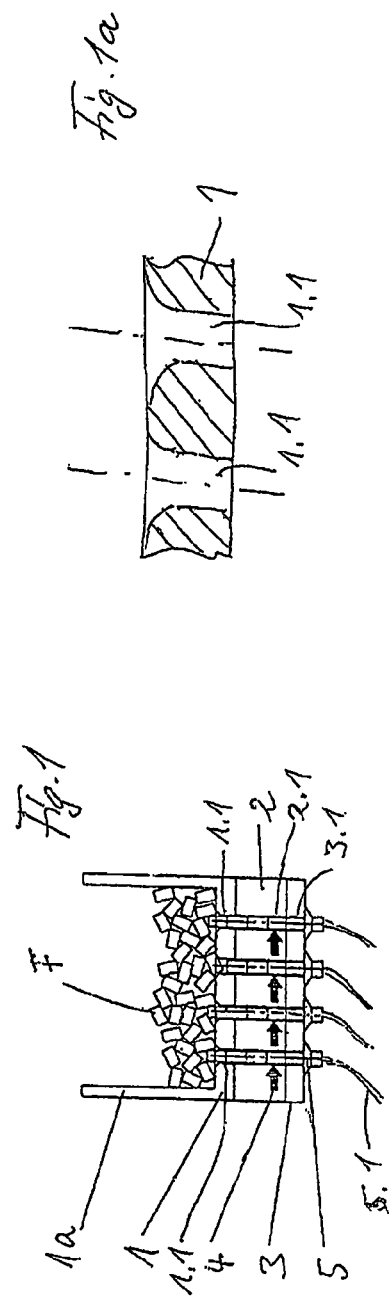
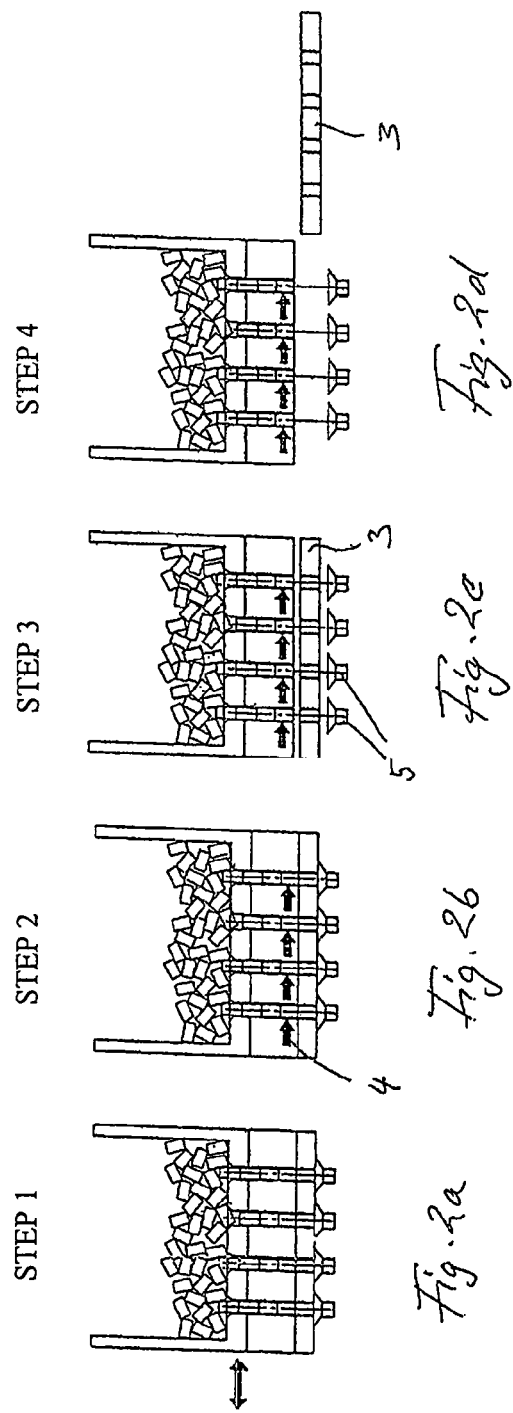

METHOD AND DEVICE FOR FITTING INJECTION-MOLDED PARTS

The invention relates to a method and apparatus for assembling injection molded parts, especially of injection molded pipette tips in which cylindrical filter elements are used.

Pipette tips are produced in larger groups by injection molding and, for example, arranged on a transfer device in an intermediate group, whereupon a predetermined group of pipette tips is transferred into a packaging unit. The pipette tips must be provided before packing with a filter in a cylindrical element wherein the filter is introduced in the tubular pipette tips so that a protection against contamination by foreign DNA or other biological, radioactive or corrosive substances is present later when using the pipette. Furthermore, such a filter element is intended to prevent the penetration of liquids and aerosol fumes into the pipette. The material of the filter elements is permeable to air but impermeable to liquids.

The fitting of the pipette tips with each having a filter element is difficult on the one hand because of the cycle time and on the other hand because of the close arrangement of the individual pipette tips in a group, for example 8×12 pipette tips in a grid of 9×9 mm.

Another problem is that different sizes and shapes of pipette tips are to be equipped with different sized filter elements with a loading device. By an exchange of the tool in the injection molding machine may be provided different shapes of pipette tips, and it is desirable not to provide a separate loading device for every form of pipette tips.

The invention has for its object to propose a method and an apparatus for fitting injection molded pipette tips, which meet the above-described requirements.

According to the invention, the cylindrical filter elements are in disorder transferred into
a collecting container, the bottom of which forms a sieve plate, wherein under the sieve buffer plate having passage openings corresponding to the sieve openings is arranged under the sieve plate. Under the buffer plate a transfer plate is disposed with corresponding recesses for accommodating the filter elements by means of which the filter elements can be moved in predetermined groups by a corresponding group of pipette tips, wherein the filter elements are transferred by an ejector in the pipette tips.

According to the invention, a method of aligning cylindrical individual elements, in particular cylindrical filter elements, for mounting of spray-cast parts, in particular provided pipette tips, comprising the steps of:
receiving the cylindrical filter elements as bulk in a receptacle container, wherein the bottom of the sieve plate with the diameter filter elements is formed with bore holes corresponding to the diameter of the filter elements,
performing a rocking motion on the receiving container for transferring the disordered filter elements in the holes of the sieve plate,
transferring the filter elements of the sieve plate into bore holes of a buffer plate,
keeping the filter elements in a predetermined position in the holes of the buffer plate, transferring the filter elements from the buffer plate into the bore holes of a transfer plate, until all bore holes of the buffer plate are occupied with a filter element, and transferring the filter elements arranged in groups in the transfer plate arranged to a handling device or another workstation.

In the buffer plate, the filter elements are advantageously held by a controllable retaining device until all the holes of the buffer plate are occupied by at least one filter element. Advantageously, the retaining device is formed by applying a vacuum on the periphery of the bore holes in the sieve plate, wherein said vacuum is applied controlled so that in each case only one filter element is released and a following filter element is retained.

A retaining device in the form of suction holes on the circumference of the bore holes in the buffer plate allows a high density of the receiving bores in the buffer plate per unit area.

However, it is also possible to provide a mechanical retaining means, in which a movable member engages radially in the bore hole in the buffer plate and is again retractable. Also, such mechanical element may be controlled by application of compressed air and vacuum.

It is possible to provide a ring inflatable by air pressure in a bore hole in the buffer plate or at the end of a bore hole in the buffer plate, wherein a filter element is held by reducing the inner diameter of the elastic ring and the filter element is released by radially expanding the ring by application of a vacuum.

After filling of the transfer plate with filter elements, the transfer plate is preferably raised from the buffer plate and moved on to a handling device, wherein the transfer plate has a predetermined group of receiver openings corresponding to the set of holes in the buffer plate.

The degree of filling of the buffer plate is preferably monitored by the sensor elements, which are provided on the underside of the transfer plate and are lifted when moving the transfer plate to a handling device by the transfer plate.

To accelerate the transfer of the filter elements from the buffer plate into the transfer plate preferably vacuum can be applied to the transfer plate.

A device for aligning elements, in particular filter elements, for fitting injection molded parts, in particular pipette tips, has according to the invention a receptacle container for receiving the filter elements in the bulk, further, a sieve plate forming the bottom of the receptacle container with bore holes for receiving individual filter elements, wherein a buffer plate is deposed below the sieve plate and at the buffer plate has bore holes corresponding to the bore holes in the sieve plate. Buffer plate and perforated sieve plate perform advantageously together a shaking out motion, while a transfer plate disposed under the buffer plate remains stationary. The transfer plate with bore holes corresponding to the bore holes of the buffer plate is positioned movable relative to the
buffer plate and disposed under the buffer plate.

Based on the separate formation of screen plate, buffer plate and transfer plate, these components can be easily replaced when other sizes of filter elements are to be processed.

Advantageously, the orifices of the bore holes in the perforated sieve plate are funnel-shaped and provided in particular with rounded edges to facilitate alignment of the filter elements in the bore holes of the sieve plate.

The thickness dimension of the screen plate or the length of the bore holes in the sieve plate is preferably constructed larger than the length of a filter element.

The buffer plate can advantageously have a thickness dimension which is greater than the longitudinal dimension of a filter element, so that the buffer plate cannot only take a single filter element, a retaining device is provided at the individual bore holes in the buffer plate which receives a filter element in a predetermined position and controlled releases the filter element.

Advantageously, in each case, a sensor element is disposed under each bore hole of the transfer plate to monitor the degree of filling of the transfer plate.

Here, a connection may be provided for applying a vacuum to each bore hole of the transfer plate.

For a fast clock sequence, the transfer plate is preferably be constructed as a rotating plate, wherein groups of bore holes on the periphery of the rotatable plate are formed for receiving of filter elements, wherein the filter elements can be removed from the bore holes by way of a handling device. For example, the handling device can employ pressure or vacuum to remove the filter elements.

Figure 4:
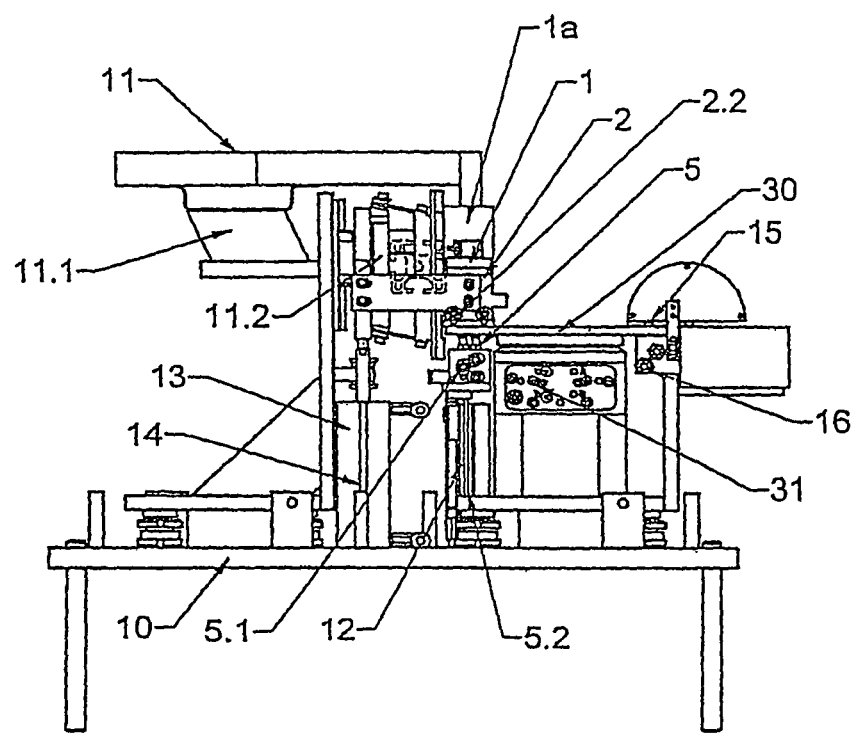
Figure 5:
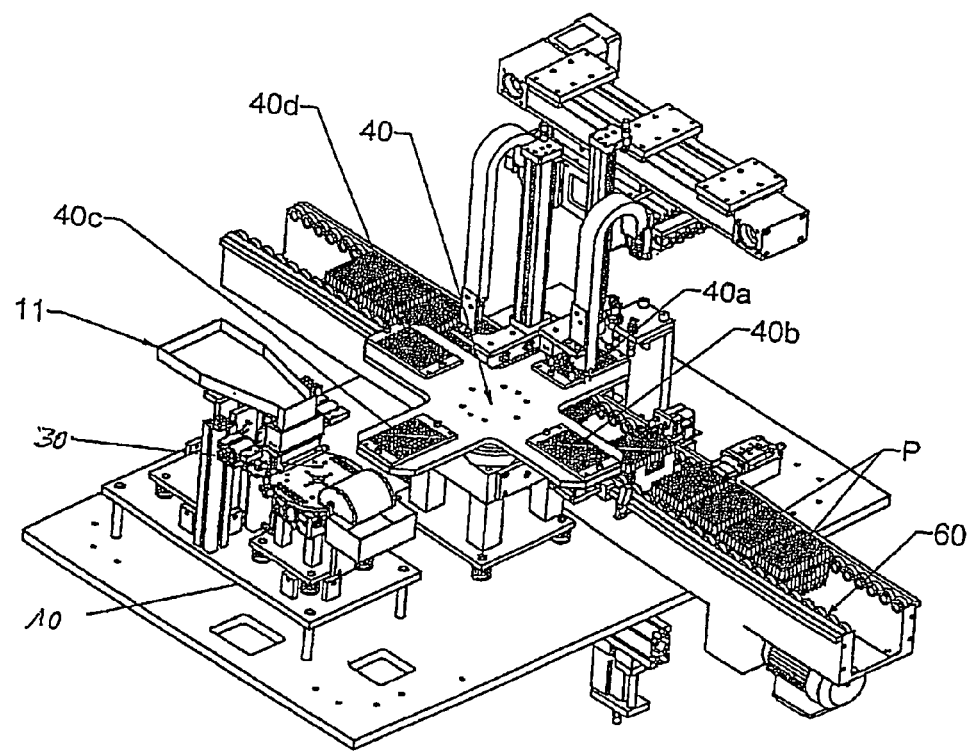

Further advantages are set forth in the following description and in the other claims. The invention is for example explained in detail with reference to the drawings. It is shown in:

FIG. 1 is a schematic representation of the construction of a separating device, FIG. 2 individual steps of transferring the filter elements onto a transfer plate, FIG. 3 is an exploded view of a separating device, FIG. 4 is a side view of a possible construction of the separating device, and FIG. 5 is a perspective view of a loading device.

FIG. 1 shows a schematic sectional view of a receptacle container 1a in pot shape, the bottom of which is formed as a sieve plate 1 with openings 1.1. The diameter of the apertures or, respectively, the sieve openings 1.1 is matched to the diameter of the cylindrical filter elements F, which are filled as bulk material in the receptacle container shown schematically in FIG. 1.

The receptacle container 1a, integrally formed as a sieve plate 1 in FIG. 1 and FIG. 2, is preferably configured as two parts as shown in FIG. 3.

The transition of the surface of the sieve plate 1 in the sieve openings 1.1 is approximately a funnel-shaped construction, preferably with rounded edges, like the detail representation in FIG. 1a shows, so that the cylindrical filter elements F by a shaking movement of the sieve plate 1 can be more easily aligned and directed in a horizontal direction and optionally also be more easily aligned in a vertical direction in FIG. 1 on the sieve openings 1.1, and introduced into the sieve openings 1.1.

The sieve plate 1 has a predetermined thickness dimension in relation to the length of the filter elements F. Preferably, the thickness of the sieve plate 1 is slightly larger than the length of the filter elements F to be separated.

The filter elements F can have a longitudinal dimension which is greater than the diameter, but it is also possible to process relatively short filter elements with a diameter that is greater than the longitudinal dimension in the axial direction of the filter element.

The diameter of the sieve openings 1.1 is this way matched to the diameter of the filter elements F, that the diameter of the sieve opening is slightly larger than the diameter of a filter element F, so that it can slide in the sieve bore hole downwardly by gravity.

A buffer plate 2 with openings or, respectively, bore holes 2.1 corresponding to the sieve openings 1.1 is provided below the sieve plate 1 such that filter elements F entered into the sieve openings 1.1 can enter the bore holes 2.1 of the buffer plate 2 unimpeded. The bore holes 2.1 in the buffer plate 2 thus form an extension of the bore holes 1.1 of the sieve plate.

The thickness of the buffer plate 2 is larger constructed as the length of a single filter element F. A retaining device generally designated with 4 in FIG. 1 is provided on each individual bore hole 2.1 through which the retaining device holds the filter elements F in the individual bore holes 2.1 such that the filter elements can be held in the individual bore holes 2.1 of the buffer plate 2 at a predetermined height level by a vacuum laterally applied to the bore holes 2.1 or on the periphery of the bore holes such that the filter elements F cannot exit downwardly.

The retaining device 4 can for example be formed such that the filter elements can be held in the individual bore holes 2.1 of the buffer plate 2 through a vacuum applied on the side at the bore holes 2.1 or, respectively, at the circumference of the bore holes.

Also a mechanical retaining device 4 is possible in which one element engaging in the bore hole from a side holds a filter element F in a predetermined position and releases the filter element by a lateral withdrawal.

Such elements can be controlled by a common actuator.

Preferably, suction port openings are furnished on the periphery of the bore holes 2.1 and the vacuum is applied through the suction port openings. In this way a dense packing of bore holes 2.1 per unit area is possible because a space-saving receptacle container 4 can be formed by channels in the buffer plate 2.

These suction openings on the circumference of the bore holes 2.1 of the buffer plate can be round or slit-shaped, wherein slots extending in an axial direction of the bore holes can be matched and tuned to the length of a filter element in the axial direction of the bore holes.

It is also possible to provide suction hole openings only over a part of the periphery, so that a filter element is held in the bore hole 2.1 by vacuum, for example, on a half of the circumference.

When shaking the sieve plate 1, the buffer plate 2 is also moved, so that existing filter elements are not pinched at the transition point between sieve plate and buffer plate.

A transfer plate 3 with receiving bores 3.1 in accordance with the bore holes in the sieve plate and buffer plate is arranged below the buffer plate 2. This transfer plate 3 is used for loading the filter elements F to a transfer station, which will be explained in more detail below.

A sensor element 5, for example, a vacuum sensor, is disposed below the transfer plate 3 in the region of each receiving bore hole 3.1 and determines the presence of a filter element F in the associated bore hole 2.1 of the buffer plate 2.

The thickness of the transfer plate 3 substantially corresponds to the length of a filter element F, but it is not necessary to match exactly the thickness of the transfer plate to the length of a filter element.

It can be determined through the sensor elements 5 whether already a filter element F is in the individual bore holes in the supply position of the retainer device 4 at the individual bore hole 2.1 of the buffer plate 2. Once every bore hole 2.1 of the buffer plate 2 is provided with a filter element F, the retention function of the retainer device 4 is canceled, so that in each case one filter element F can get out of each bore hole 2.1 and pass into the transfer plate 3. After release of a single filter element F in the bore hole 2.1 of the buffer plate 2, the retention function is activated again, so that only one filter element can be transferred into the transfer plate 3.

The length of the bore holes 2.1 in the buffer plate 2 can be constructed to be larger than the length of a filter element, so that in conjunction with the sieve bore 1.1 in the sieve plate 1 several filter elements can be stacked. In order to separate the filter elements disposed in a sieve bore hole 1.1 and a bore hole 2.1 of the buffer plate 2 to separate located ends filter elements for the transition to the transfer plate 3, the retainer device 4 is controllable formed in the buffer plate 2 that in each case only one filter element is released and the next following filter element is retained again. In the case of a retaining device 4 by means of vacuum, the application of a vacuum can be briefly interrupted, so that a filter element is released and by gravity falls down while the next following filter element is held back in a predetermined position by re-applying a vacuum.

However, it is also possible to provide superposed suction openings on the periphery of the bore holes 2.1, wherein the suction openings in the axial direction of the bore holes 2.1 have such a distance from each other that the lower suction openings are lying on the periphery of a filter element, while the overlying suction openings are disposed opposite to a subsequent filter element. In this way a vacuum can remain applied to the upper suction openings, while at the lower suction openings the vacuum application is stopped, so that the filter element can slide downwards. Then the negative pressure at the upper suction openings is interrupted and is applied to the lower suction openings so that the subsequent filter element is held in the predetermined provision for the transfer into the transfer plate 3.

In a corresponding manner a mechanical retention device can engage not only on a lower filter element in a sieve plate 2 but also on a filter element disposed above in the bore hole 2.1 of the buffer plate 2.

Preferably, the sensor elements 5 are connected to a suction device upon eliminating the retaining function so that the individual filter elements F are transferred by suction into the transfer plate 3. FIG. 1 shows at 5.1 only schematically the connection of the individual sensor elements 5 to a vacuum device, not shown, can be cyclically controlled, so that for a short time vacuum is applied depending on the release of the retaining function.

FIG. 2a illustrates the first step of the separating device of FIG. 1, wherein the components 1 and 2 in FIG. 1 perform a rocking motion in a horizontal direction as indicated by a double arrow in FIG. 2a. In addition to a horizontal shaking movement, a slight oscillation can be superposed in the vertical direction to facilitate the insertion of the individual filter elements F into the sieve bore holes 1.1.

Already during the shaking movement in FIG. 2a, the retaining function of the retaining device 4 is enabled so that the filter elements F reach the individual bore holes 2.1 of the buffer plate 2 only up to the retaining of the retaining device 4.

The transfer plate 3 is preferably not moved during the shaking motion of the separating device.

Once it is determined by the sensors 5 that all bore holes 2.1 of the buffer plate 2 are filled with at least one filter element F, the shaking motion is stopped and the retention function is released so that a single filter element F of each bore hole 2.1 of the buffer plate 2 can be transferred into the transfer plate 3, as reproduced according to a second step as shown in FIG. 2b.

After filling of the transfer plate 3 in a third step of FIG. 2c, the sensor elements 5 are lifted from the transfer plate 3. At the same time or thereafter the transfer plate 3 is lifted from the buffer plate 2 in order to initiate the transfer to a transfer station.

Preferably, means are also provided in the transfer plate 3, which means hold the filter elements F in the mounting bore holes 3.1 of the transfer plate 3. For this purpose, for example, the inner circumference of the bore holes 3.1 can be provided by roughening with a higher coefficient of friction for the filter material.

A vacuum can also be applied to the transfer plate as is done in the retaining device 4 for supporting the filter elements F. A mechanical attachment of the filter elements can also be provided in the transfer plate in the same manner.

In a practical embodiment of a holding device by means of a vacuum, a slight depression can be formed in a side wall of the bore hole in the buffer plate and in the transfer plate, wherein a vacuum bore hole joins the slight depression. The filter element is pulled and held at a side at the bore hole wall by applying a vacuum.

In a fourth step, finally, the transfer plate 3 is moved to a transfer station, as shown in FIG. 2d, shows, at the same time a further transfer plate can be positioned below the buffer plate 2, wherein at the same time for example a further transfer plate can be positioned below the buffer plate by means of a rotating plate, so that in a non-illustrated fifth step the step 1 in FIG. 2a can be initiated by attaching the second transfer plate on the buffer plate 2 and attachment of the sensing elements 5 on the second transfer plate.

FIG. 3 shows an exploded view of a separating device with a separate, frame-shaped receiving container 1a. The bottom of the receptacle container forming the sieve plate 1 is provided with a centering bore hole 1.2 wherein a corresponding centering pin engages on the underside of the receptacle container 1a. Similarly, the buffer plate 2 and the rotational plate 30, which is constructed as a transfer plate 3, can be aligned relative to each other. The rotating plate 30 has four groups of bore holes 3.1 in the periphery of the shown embodiment example, wherein in each case one group corresponds to the transfer plate 3 shown in FIG. 3.

FIG. 3 shows connectors 2.2 at the buffer plate 2 for applying a vacuum to the retainer device 4. Vacuum connections 3.2 are also provided on the rotary plate 30.

When a different shape and/or size is supplied from the pipette tips from a non-illustrated injection molding machine to be equipped with filter elements of another corresponding diameter, then the sieve plate 1, the buffer plate 2 and transfer plate 3 can be connected to the separating device and exchanged with another set of screen plate 1, buffer plate 2 and the transfer plate 3 to be replaced, which have a diameter adapted to the bore hole diameter of the new filter elements.

In this way, the separating device can be retrofitted in a simple manner to a new product line.

FIG. 4 shows a side view of an exemplary embodiment of a separating device. On a substrate 10 is indicated a feeder supply system at 11 to which the filter elements are supplied, wherein 32 filter elements can be fed, for example, with a cycle time of five seconds. The filter elements F pass from the feeder 11 through a first linear conveyor 11.1 to a second linear conveyor 11.2, wherein the receiver container 1a is filled with filter elements F from the second linear conveyor 11.2

A vacuum port is shown at 2.2 at the block shaped buffer plate 2, which vacuum port 2.2 is provided for activating the retaining device 4. The sensor elements 5 are arranged on a lifting device 12 and are provided with a vacuum connector 5.1. A position detection device for the sensor elements 5 is designated with 5.2.

13 is a lifting device which lifts the separating mechanism off the transfer plate 3 (FIG. 2c).

14 is a sensor device for position detection.

The rotary plate 30 reproduced in FIG. 3 is disposed on a rotary switching table 31. A handling device, not shown, takes out the filter elements from the bore holes of the rotating plate 30 and transfers them, for example, into an intermediate storage device of the loading device, as will be explained with reference to FIGS. 5 to 7.

FIG. 5 shows a perspective view of the separating device of FIG. 4 with the rotary plate 30 be fitted on a mounting device on which groups of pipette tips P with filter elements F are fitted.

A turntable is indicated in FIG. 5 with 40, which turntable is designated in a cross shape, and has four sets of locating bore holes for pipette tips P, where in each case a group 40a to 40d of bore holes is filled with pipette tips P. In the illustration of FIG. 5, a group 40c is completely filled with pipette tips P, taken out through a not-shown handling device of the rotary plate 30 and filter elements F are inserted into the pipette tips P.

A group of pipette tips P fitted with filter elements F is transferred from the turntable 40 onto a conveyor belt 60 on which the pipette tips P fitted with filter elements are stored in a package unit.

The invention claimed is:

1. A method for the alignment of individual elements, in particular filter elements (F), for mounting of injection molded parts, in particular the pipette tips (P), comprising the following steps:
receiving the filter elements (F) as bulk material in a receptacle container (1a), wherein the bottom of the receptacle container (1a) is formed as a sieve plate (1) with bore holes (1.1) corresponding to the diameter of the filter elements (F),
performing a rocking motion on the receiving container (1a) for transferring the disordered filter elements (F) into the bore holes (1.1) of the sieve plate (1),
transferring said filter elements (F) of the sieve plate (1) into bore holes (2.1) of a buffer plate (2),
making available said filter elements (F) in a predetermined position in the bore holes (2,1) of the buffer plate (2),
transferring said filter elements (F) of the buffer plate (2) into bore holes (3.1) of a transfer plate (3), and
transferring the filter elements (F) arranged in groups in the transfer plate (3) to a handling device, wherein
the filling degree of the buffer plate (2) is monitored on the transfer plate (3) by means of sensor elements (5).

2. The method of claim 1, wherein the filter elements (F) are held in the buffer plate (2) by a retaining device (4) until all bore holes (2, 1) of the buffer plate (2) are occupied with at least one filter element (F).

3. The method according to claim 1, wherein after filling of the transfer plate (3) with filter elements (F), the transfer plate (3) is lifted from the buffer plate (2) and is moved to a handling device.

4. The method according to claim 1, wherein the filter elements (F) can be transferred from the buffer plate (2) into the transfer plate (3) by way of a negative pressure.

5. A method for the alignment of individual elements, in particular filter elements (F), for mounting of injection molded parts, in particular the pipette tips (P), comprising the following steps:
receiving the filter elements (F) as bulk material in a receptacle container (1a), wherein the bottom of the receptacle container (1a) is formed as a sieve plate (1) with bore holes (1.1) corresponding to the diameter of the filter elements (F),
performing a rocking motion on the receiving container (1a) for transferring the disordered filter elements (F) into the bore holes (1.1) of the sieve plate (1),
transferring said filter elements (F) of the sieve plate (1) into bore holes (2.1) of a buffer plate (2),
making available said filter elements (F) in a predetermined position in the bore holes (2,1) of the buffer plate (2),
transferring said filter elements (F) of the buffer plate (2) into bore holes (3.1) of a transfer plate (3), and
transferring the filter elements (F) arranged in groups in the transfer plate (3) to a handling device, wherein
the retaining device (4) is controlled such that only one filter element in the bore hole (2.1) of the buffer plate (2) is released and the next succeeding filter element is retained.

6. An apparatus for aligning elements, especially filter elements (F), for mounting of injection molded parts, in particular pipette tips (P) comprising
a receptacle container (1a) for receiving filter elements (F) as bulk material, a bottom of the receptacle container forming a sieve plate (1) with bore holes (1.1) for receiving individual filter elements (F),
a buffer plate (2) disposed under the sieve plate (1) and having bore holes (2.1) corresponding to the bore holes of the sieve plate (1), and
a transfer plate (3), which is disposed movable relative to the buffer plate (2), is located below the buffer plate (2) and having bore holes (3.1) corresponding
to the bore holes of the buffer plate (3),
wherein
in each case a sensor element (5) is arranged below each bore hole (3.1) of the transfer plate (3).

7. The apparatus of claim 6, wherein the mouth opening of the bore holes (1,1) in the sieve plate (1) is funnel-shaped and has rounded edges.

8. The apparatus according to claim 6, wherein the sieve plate (1) has a thickness dimension which is greater than the length of a filter element (F).

9. The apparatus according to claim 6, wherein the buffer plate has a thickness dimension which is greater than the longitudinal dimension of a filter element (F) and wherein a retaining device (4) is disposed in the buffer plate (2), and wherein the retaining device (4) holds a filter element (F) in each bore hole (2,1) of the buffer plate (2) in a predetermined position.

10. The apparatus according to claim 6, wherein a connection for applying a vacuum is furnished at each bore hole (3.1) of the transfer plate (3).

11. The apparatus according to claim 6, wherein the transfer plate (3) is formed as a rotary plate (30), wherein groups of bore holes (3.1) are formed on the periphery of the rotary plate (30) for accommodating filter elements (F).

12. The apparatus of claim 11, wherein a handling device (15) is placed on the circumference of the rotary plate (30) for the removal of the filter elements (F) from the rotating plate (30).

13. The apparatus according to claim 9, wherein the retaining device (4) exhibits suction bore holes on the periphery of the receiver bore holes (2.1) of the buffer plate (2), wherein a vacuum can be controllably applied through the receiver bore holes (2.1).

14. The apparatus according to claim 13, wherein the retaining device (4) is controlled such that only one filter element in the bore hole (2.1) of the buffer plate (2) is released and the next succeeding filter element is retained.

* * * * *